(12) United States Patent
Murphy

(10) Patent No.: US 10,004,752 B2
(45) Date of Patent: Jun. 26, 2018

(54) ADAPTER FOR ACETABULAR COMPONENT POSITIONING

(71) Applicant: Stephen B. Murphy, Winchester, MA (US)

(72) Inventor: Stephen B. Murphy, Winchester, MA (US)

( * ) Notice: Subject to any disclaimer, the term of this patent is extended or adjusted under 35 U.S.C. 154(b) by 0 days. days.

(21) Appl. No.: 13/692,270

(22) Filed: Dec. 3, 2012

(65) Prior Publication Data

US 2013/0164075 A1 Jun. 27, 2013
US 2014/0255084 A9 Sep. 11, 2014

Related U.S. Application Data

(63) Continuation-in-part of application No. 12/134,545, filed on Jun. 6, 2008, now Pat. No. 8,267,938.

(60) Provisional application No. 61/566,350, filed on Dec. 2, 2011, provisional application No. 60/984,425, filed on Nov. 1, 2007.

(51) Int. Cl.
| | |
|---|---|
| *A61B 17/58* | (2006.01) |
| *A61B 17/60* | (2006.01) |
| *A61F 2/00* | (2006.01) |
| *A61K 31/555* | (2006.01) |
| *F16C 11/10* | (2006.01) |
| *A61B 90/11* | (2016.01) |
| *A61B 17/17* | (2006.01) |
| *A61K 45/06* | (2006.01) |

(Continued)

(52) U.S. Cl.
CPC ........ *A61K 31/555* (2013.01); *A61B 17/1746* (2013.01); *A61B 90/11* (2016.02); *A61K 31/409* (2013.01); *A61K 31/44* (2013.01); *A61K 45/06* (2013.01); *F16C 11/10* (2013.01); *Y10T 403/32426* (2015.01)

(58) Field of Classification Search
CPC ... A61B 17/1746; A61B 19/201; F16C 11/10; Y10T 403/32426; A61K 45/06; A61K 31/44; A61K 31/409; A61K 31/555
USPC ......... 403/104–106; 600/53, 54, 63; 606/73, 606/81, 86–91, 99, 102; 623/17.11–17.16, 22.11–22.37
See application file for complete search history.

(56) References Cited

U.S. PATENT DOCUMENTS

| | | | |
|---|---|---|---|
| 3,457,651 A | 7/1969 | Kaeck | |
| 5,056,523 A * | 10/1991 | Hotchkiss, Jr. .... | A61B 17/3403 378/37 |

(Continued)

FOREIGN PATENT DOCUMENTS

| | | |
|---|---|---|
| JP | 2004-89653 A | 3/2004 |
| JP | 2005-111257 A | 4/2005 |

(Continued)

OTHER PUBLICATIONS

English Description of Japanese Publication No. JP2004-089,653, retrieved on Aug. 27, 2014, pp. 1-30.

(Continued)

*Primary Examiner* — Amber Anderson
*Assistant Examiner* — Nahid Amiri
(74) *Attorney, Agent, or Firm* — Cesari and McKenna, LLP; Michael R. Reinemann

(57) ABSTRACT

An adapter for a tripodal stereotactic reference frame for use in arthroplastic surgery mounts a third leg of the frame at an angle with respect to the other two legs to facilitate use of said frame with varying surgical exposures.

15 Claims, 4 Drawing Sheets

(51) Int. Cl.
*A61K 31/409* (2006.01)
*A61K 31/44* (2006.01)

(56) References Cited

U.S. PATENT DOCUMENTS

| | | | |
|---|---|---|---|
| 5,086,401 A | | 2/1992 | Glassman et al. |
| 5,122,145 A | | 6/1992 | Fishbane |
| 5,141,512 A | * | 8/1992 | Farmer et al. ............... 606/87 |
| 5,327,907 A | | 7/1994 | Fischer |
| 5,376,093 A | | 12/1994 | Newman |
| 5,515,616 A | | 5/1996 | Merkin |
| 5,697,939 A | * | 12/1997 | Kubota et al. .............. 606/130 |
| 5,776,143 A | * | 7/1998 | Adams ......................... 606/130 |
| 5,824,007 A | * | 10/1998 | Faraz et al. ................. 606/130 |
| 5,916,219 A | * | 6/1999 | Matsuno et al. ............... 606/88 |
| 6,090,114 A | * | 7/2000 | Matsuno et al. ............... 606/88 |
| 6,132,437 A | * | 10/2000 | Omurtag et al. ............ 606/130 |
| 6,228,089 B1 | | 5/2001 | Wahrburg |
| 6,290,196 B1 | * | 9/2001 | Mayenberger ............ 248/274.1 |
| 6,314,312 B1 | | 11/2001 | Wessels et al. |
| 6,395,005 B1 | * | 5/2002 | Lovell ............................. 606/91 |
| 6,634,883 B2 | * | 10/2003 | Ranalli ................. A61C 19/04 433/50 |
| 7,182,766 B1 | | 2/2007 | Mogul |
| 7,201,756 B2 | * | 4/2007 | Ross et al. ....................... 606/96 |
| 7,344,542 B2 | * | 3/2008 | Collazo et al. ................. 606/88 |
| 7,419,492 B2 | | 9/2008 | Yoon et al. |
| 7,651,501 B2 | * | 1/2010 | Penenberg et al. ............. 606/91 |
| 8,267,938 B2 | | 9/2012 | Murphy |
| 8,986,309 B1 | | 3/2015 | Murphy |
| 2003/0153829 A1 | * | 8/2003 | Sarin et al. ................... 600/426 |
| 2004/0152970 A1 | | 8/2004 | Hunter et al. |
| 2004/0210233 A1 | | 10/2004 | Yoon et al. |
| 2004/0254586 A1 | | 12/2004 | Sarin et al. |
| 2004/0260312 A1 | | 12/2004 | Magnusson et al. |
| 2005/0076441 A1 | | 4/2005 | Dominati et al. |
| 2005/0107799 A1 | | 5/2005 | Graf et al. |
| 2005/0234332 A1 | | 10/2005 | Murphy |
| 2006/0025778 A1 | | 2/2006 | Ferree |
| 2006/0052795 A1 | | 3/2006 | White |
| 2006/0100504 A1 | | 5/2006 | Jansen et al. |
| 2006/0161167 A1 | * | 7/2006 | Myers et al. .................... 606/91 |
| 2006/0184177 A1 | | 8/2006 | Echeverri |
| 2006/0225529 A1 | | 10/2006 | Fischer et al. |
| 2006/0241441 A1 | | 10/2006 | Chinn |
| 2009/0163922 A1 | | 6/2009 | Meridew et al. |
| 2009/0171370 A1 | | 7/2009 | Yoon et al. |
| 2009/0306679 A1 | | 12/2009 | Murphy |
| 2011/0196433 A1 | | 8/2011 | Kleiner |
| 2012/0245647 A1 | | 9/2012 | Kunz et al. |
| 2013/0006255 A1 | | 1/2013 | Murphy |
| 2015/0289891 A1 | | 10/2015 | Murphy |

FOREIGN PATENT DOCUMENTS

| | | |
|---|---|---|
| JP | 2006-501972 A | 1/2006 |
| SU | 441 933 | 9/1974 |
| WO | WO 00/30557 | 6/2000 |
| WO | WO 01/34017 | 5/2001 |
| WO | WO 03/009768 | 2/2003 |
| WO | WO/2004/021898 | 3/2004 |
| WO | WO/2005/046451 | 5/2005 |
| WO | WO-2006/109983 A1 | 10/2006 |

OTHER PUBLICATIONS

English Description of Japanese Publication No. JP 2005-111,257, retrieved on Aug. 27, 2014, pp. 1-26.

English Translation of Office Action, from Japanese Patent Office for Japanese Patent Application No. JP 2013-112536, dated Apr. 1, 2014, pp. 1-2.

European Search Report, European Application No. 13153277.2-1659 / 2626032, Applicant: Stephen B. Murphy, Date of Mailing: Mar. 20, 2014, pp. 1-6.

European Search Report, European Application No. 13153236.8-1659 / 2626031, Applicant: Stephen B. Murphy, Date of Mailing: Aug. 22, 2014, pp. 1-5.

Notification of Transmittal of the International Search Report and the Written Opinion of the International Searching Authority, or the Declaration, International Filing Date: Oct. 30, 2008, International Application No. PCT/US2008/012300, Applicant: Stephen B. Murphy, Date of Mailing: Mar. 5, 2009, pp. 1-8.

Archibald, H. A. P., et al., "The Transverse Acetabular Ligament: An Aid to Orientation of the Acetabular Component During Primary Total Hip Replacement: A Preliminary Study of 1000 Cases Investigating Postoperative Stability," British Editorial Society of Bone and Joint Surgery, Journal Bone Joint Surgery, vol. 88-B, No. 7, Jul. 2006, pp. 883-886.

Chow, JC, et al., "Evaluation of Intraoperative Pelvic Positioning Using Software-based Computed Tomography/Radiography Matching," International Society for Computer Assisted Orthopedic Surgery, Jun. 2008, pp. 192-194.

Klingenstein, G., et al., "Pelvic Tilt Before and After Total Hip Arthroplasty," International Society for Computer Assisted Orthopedic Surgery, Jun. 2008, pp. 99-100.

* cited by examiner ered in the lateral position, where the
ADAPTER FOR ACETABULAR COMPONENT POSITIONING The present application claims the benefit of U.S. Provisional Patent Application Ser. No. 61/566,350, which was filed on Dec. 2, 2011, by Stephen B. Murphy for an ADAPTOR FOR ACETABULAR COMPONENT POSITIONING and is hereby incorporated by reference.

This application is a continuation-in-part of U.S. patent application Ser. No. 12/134,545, "Method And Apparatus For Determining Acetabular Component Positioning", filed Jun. 6, 2008 by Stephen B. Murphy, now issued as U.S. Pat. No. 8,267,938, which application claims the benefit of U.S. Provisional Patent Application Ser. No. 60/984,425, filed Nov. 1, 2007, and the entire contents of which are expressly incorporated herein by reference.

BACKGROUND OF THE INVENTION

Background Information

The above application ("the '545 application") describes a method and apparatus for determining acetabular component positioning, particularly for use in connection with hip arthroplasty. The method establishes a coordinate frame for the ipsilateral hip, and an apparatus is disclosed that rapidly and reliably establishes the desired frame. A preferred form of the apparatus is shown in FIG. 4 of the '545 application, and comprises a manual stereotactic instrument in the form of a tripod having of a pair of extensible arms extending from a common hub about which the arms can be rotated. First and second legs or cannulas, respectively, extend from an end of the respective arms remote from the hub and generally perpendicular to the plane formed by the arms, and a third leg or cannula extends from the hub, also generally perpendicular to that plane. The tips of the legs remote from the plane themselves are then positioned by the surgeon or by the instrument itself.

One of the tips is placed at the root of the ischium, a short distance (e.g., 20 millimeters or so) above the infracotyloid notch; this establishes a "basepoint" of Anchor point for proper docking of the instrument to the hip. A second tip is placed by the surgeon on the lateral side of the iliac wing, adjacent to the anterior superior iliac spine. The third tip then lands on the surface of the lateral ilium, anterior to the sciatic notch; the precise location is determined by the settings of the instrument, in particular, the extensions of the arms and the angle between them. The tips of the three legs, when so positioned, themselves form a plane and provide a reference frame with respect to which the orientation of the hip may be referenced. The procedure is fast and accurate, and has significantly improved the accuracy of acetabular component positioning. Further details are set forth in the '545 application.

The above configuration is especially useful for procedures in which a patient is oriented in the lateral position. In that position, the instrument readily accommodates to the three commonly used lateral exposures, namely, the posterior exposure, the superior capsulotomy, and the transgluteal exposure. In these exposures, the desired basepoint can readily be observed and directly reached. However, other operative exposures can present difficulties. For example, some surgeons prefer to use an anterolateral exposure for arthroplasty. In this exposure, the gluteus medium and minimus muscles and femur are retracted posteriorly instead of anteriorly, and therefore these muscles, together with skin and subcutaneous tissue, lie in the path of the basepoint cannula.

SUMMARY OF THE INVENTION

As discussed above, the configuration of FIG. 4 of the '545 application is especially useful for exposures in which the patient is oriented in the lateral position, where the desired basepoint for fixing one of the legs of the instrument can readily be observed and directly reached. (As used herein and in the claims, the term "leg" should be understood to encompass not only solid legs, but hollow legs such as cannulas as well). However, in other operative exposures used in hip arthroplasty, such as an anterolateral exposure, the positioning of skin, muscles and tissue obstruct direct access to a desired basepoint or Anchor point, which is preferably located in the region of the ischium as it joins the lower wall of the acetabulum. I have resolved this problem by enabling repositioning of the basepoint leg so that it may approach the desired basepoint at an angle to that at which it would otherwise approach it, thus avoiding the obstructions otherwise interposed by the anterolateral exposure.

Accordingly, it is an object of the invention to extend the capabilities of the method and apparatus of the '545 application to encompass a greater variety of surgical exposures Further, it is an object of the invention to extend the capabilities of the method and apparatus of the '545 application to encompass surgical exposures in which access to the desired basepoint is at least partially blocked or restricted.

The foregoing and other and further objects and features of the present invention will be understood on reference to the following detailed description of the invention, when taken in conjunction with the accompanying drawings, in which.

DETAILED DESCRIPTION OF AN ILLUSTRATIVE EMBODIMENT

Figure 1:
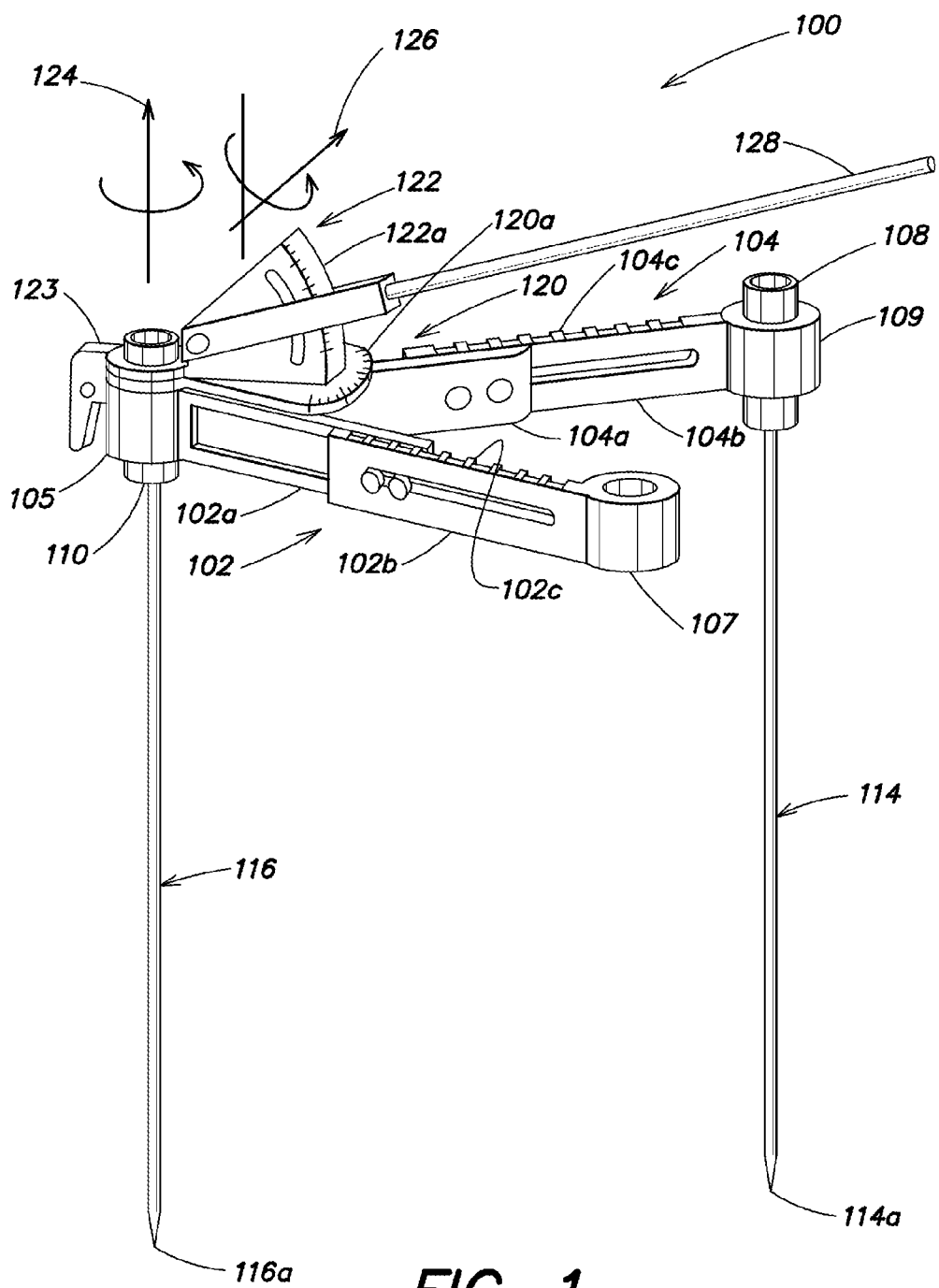
FIG. 1 is a modified version of FIG. 4 of the '545 application.
Figure 4:
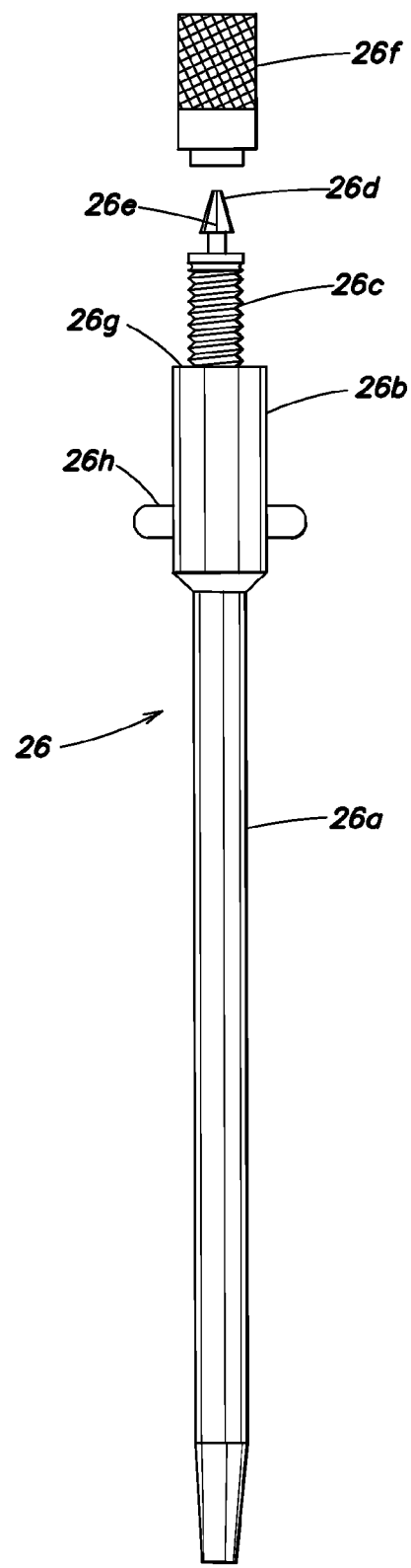
FIG. 4 shows one form of leg for mounting on adapter 10.

Turning now to FIG. 1, a modified version of FIG. 4 of the '545 patent application is shown. The reference numbers of that application have been retained for ease of reference to it. Basically, the figure shows a manual stereotactic instrument 100 in the form of a tripod having of a pair of extensible arms 102, 104 extending from a common hub 105 about which the arms can be rotated. Hollow bore conduits 107 and 109 are carried on the ends of arms 102 and 104, respectively, as well as at the hub 105 which itself includes a hollow bore conduit. Legs or cannulas 114, 116, extend downwardly from conduits 109, 105, respectively. The legs 114, 116 have tips 114a, 116a, respectively. The arms 102 and 104 are formed from first and second arm segments 102a and 104a, respectively, fixed to and extending from the hub 105. Markers 102c, 104c on the arm segments 102b, 104b, respectively, indicate the amount of extension of the arm segments, and thus the length of the arms. A rod segment 108 is snugly but removably press-fit into the hollow bore conduit 107. A first plate 120 is fixed to the hub 105. A second plate 122 is pivotally mounted on the hub 105 for rotation in the horizontal plane about a vertical axis 124 with respect to the first plate 120. A releasable lock 123 fixes the angular orientation of the plate at the orientation set by the surgeon. A guide 128 is pivotally mounted on the second plate 122 for rotation in the vertical plane about a horizontal axis 126. The first plate 120 has a scale 120a for indicating the angular orientation of the second plate 122 with respect to it (the azimuthal angle). Similarly, second plate 122 has a scale 122a for indicating the angular orientation of the guide 128 with respect to the second plate 122 (the elevation angle).

Figure 2:
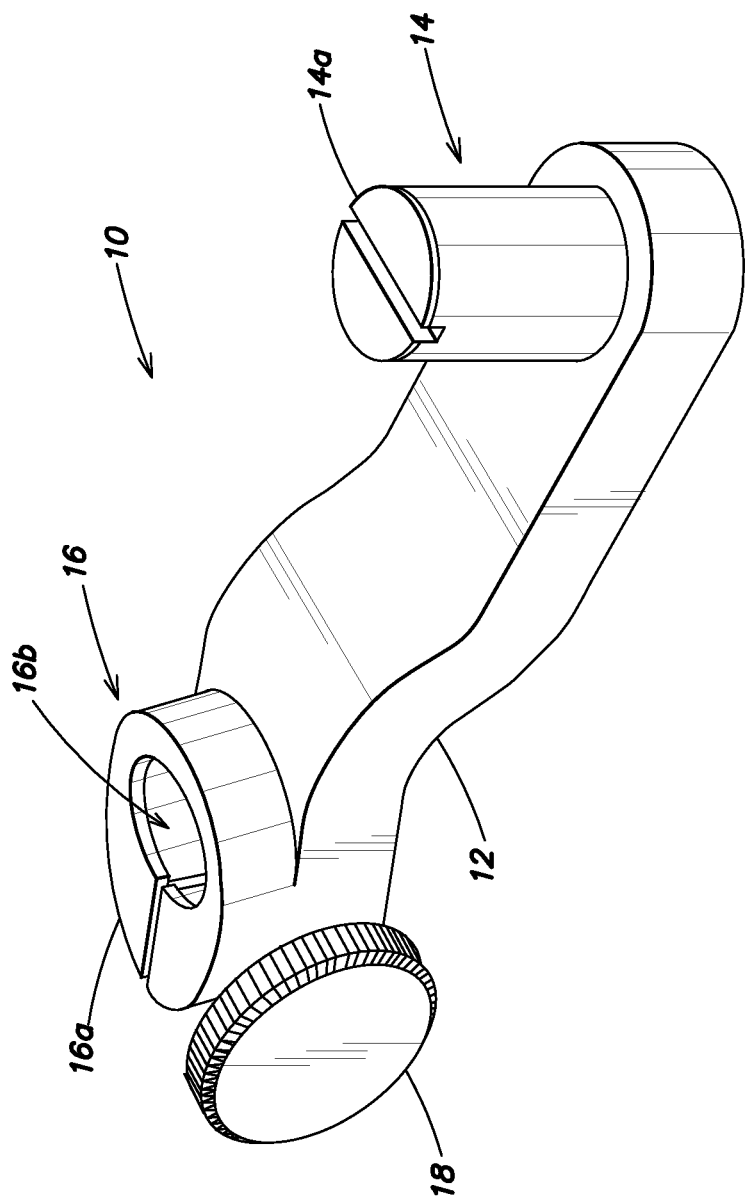
FIG. 2 is a view in perspective of a preferred embodiment of a basepoint adapter as described herein.

In the preferred embodiment of FIG. 4 of the '545 application, these legs are parallel to each other and are perpendicular to a plane formed by the arms 102, 104. In that application, a third leg or cannula 112 is fitted into, and extends downwardly from, the conduit 107, parallel to the legs or cannulas 114, 116. In accordance with the present invention, however, the leg 112 and its accompanying rod segment 106 of FIG. 4 of the '545 application is not used; accordingly, it has been removed as shown in FIG. 1 of the present application. In its place I insert an adapter, a preferred form of which is shown in FIG. 2.

The adapter 10 comprises an arm 12 having a first connector 14 at one end thereof and a second connector 16 at the other end. In the embodiment shown, the connector 14 takes the form of a cylindrical plug which is fixed to arm 12 by a screw 20 inserted through the bottom of arm 12 into the bottom of connector 14; see FIG. 3. The connector 16 has a split collar 16a having a bore 16b extending through it. A leg or cannula will be inserted into the collar 16, and will be held firmly in it on tightening a thumbscrew 18 which compresses slit 16a.

Figure 1A:
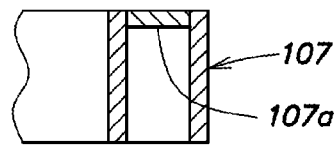
FIG. 1A is a partial sectional view of conduit 107.

In use, the connector 14 is inserted into the bottom of conduit 109, and held there by any of a number of well-known means, such as by a set-screw of the like. In order to seat the connector at a fixed distance into the conduit 107, the conduit preferably has an inner lip 107a against which the top face 14a of connector 14 butts when inserted into it; see FIG. 1A.

Figure 3:
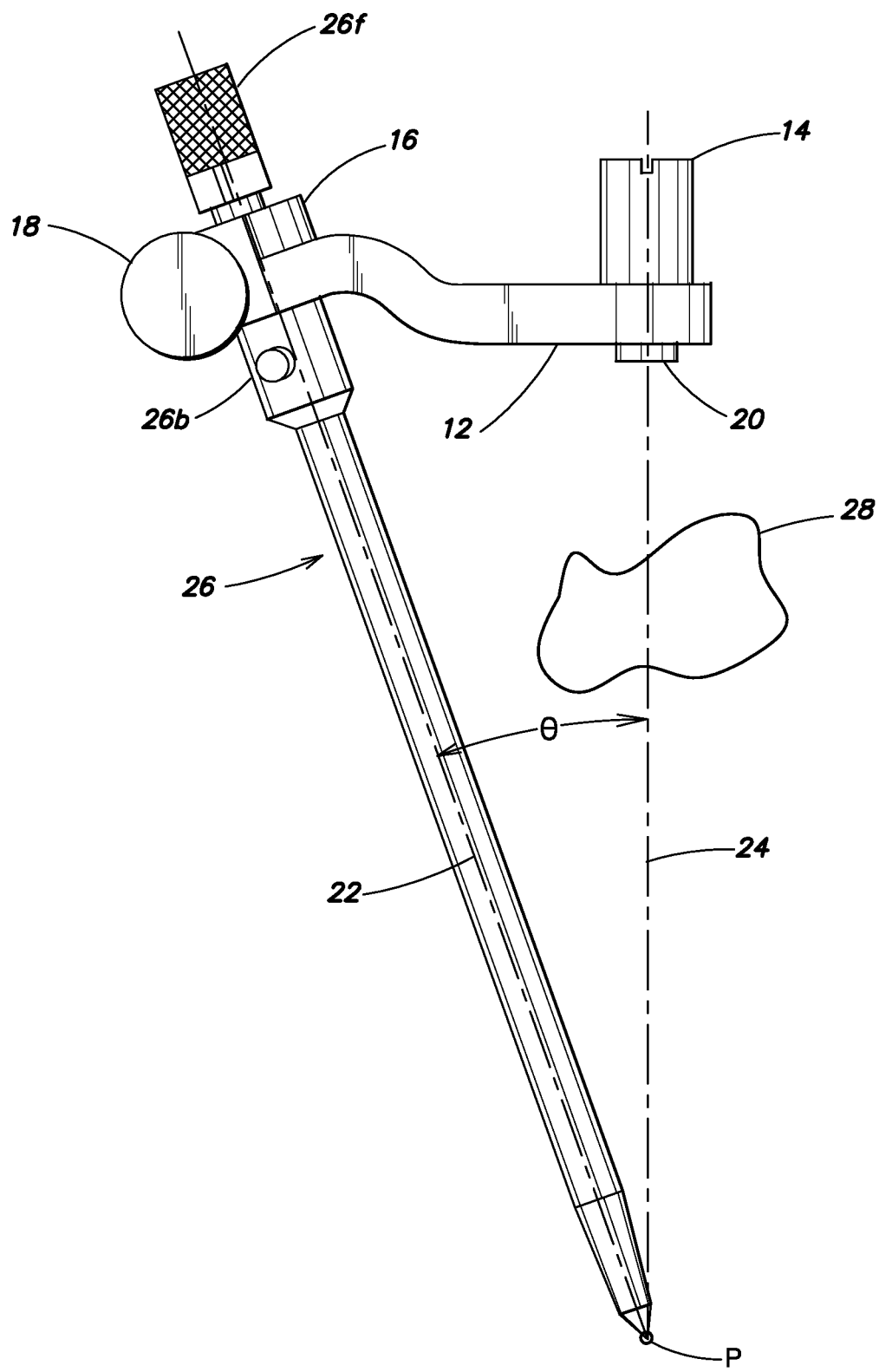
FIG. 3 is a side view of the adapter of FIG. 2 on which a cannula has been mounted.

As seen more readily in FIG. 3, arm 12 has a curved, sinuous shape. As a result, an axis 22 extending along the centerline of collar 16 is oriented at an angle θ with respect to an axis 24 extending along the centerline of connector 14. For anterolateral arthroplasty procedures, I have found that an angle of from approximately 20 to 30 degrees is appropriate. Further, these axes are coplanar, and converge to a point P. This is the basepoint or Anchor point described in the '545 application. Thus, when connector 14 is mounted on conduit 107, a leg or cannula 26 mounted on connector 14 can be directed to the same point P (FIG. 3) as one that would have been directed to that point along the axis 24 had there been no intervening muscles, skin, tissue, etc. (indicated figuratively as element 28) blocking access along axis 24. Accordingly, the instrument described in the '545 application for arthroplasty procedures using a lateral exposure can readily be adapted to accommodate arthroplasty procedures using an anterolateral exposure.

FIG. 4 shows one form of leg or cannula for mounting on adapter 10. Cannula 26 has an elongated hollow body 26a extending from and through a shoulder 26b. The upper end of the cannula is threaded, 26c, and connects to a ferrule 26d having one or more compression slits 26e in it. An internally threaded cap 26f mates with the threads 26c when assembled. Cannula or leg 26 is mounted on arm 12 by sliding it upwardly (referring to FIG. 3) through the aperture 16b of collar 16 until shoulder 26g of cannula or leg 26 butts against the bottom of arm 12. Cap 26f is then inserted over ferrule 26d onto threads 26c, the cap being rotated until the ferrule is compressed sufficiently to secure the cannula or leg 16 onto the arm. Protuberances 26h provide a grip to assist in securing and releasing the cannula or leg 26.

CONCLUSION

It will be understood that the foregoing description and drawings are directed to a preferred embodiment of the adapter, and that other forms of the adapter will readily be constructed, given the description of the issues and the formulation of the solution set forth herein, it being understood that the foregoing is intended as illustrative only as to the problem and its solution, the scope of the invention being more fully defined in the claims appended hereto.

What is claimed is:

1. A surgical instrument for establishing a reference plane for a human body structure, the surgical instrument comprising:
    a frame having a hub, a first arm, and a second arm, the first and second arms extending out from the hub and having respective ends disposed opposite the hub, the frame, including the hub and the first and second arms, defining a nominal plane having an upper surface and a lower surface;
    a guide mounted to said frame on the upper surface of the nominal plane, said guide configured to define an axis in space relative to the reference plane;
    a first leg extending from the hub of said frame;
    a second leg extending from the end of the first arm of the frame;
    an offset adapter having first and second connectors, the first connector of the offset adapter attached to the end of the second arm of the frame; and
    a third leg attached to the second connector of the offset adapter, wherein
        said first, second, and third legs extend from the lower surface of the nominal plane defined by said frame,
        said first, second, and third legs have respective tips opposite the frame,
        said first and second legs extend substantially orthogonal to the nominal plane defined by said frame such that the tip of said first leg is aligned with the hub and the tip of said second leg is aligned with the end of the first arm,
        the first and second connectors of said offset adapter are spaced from each other such that said third leg extends at a predetermined angle to the nominal plane defined by said frame, and the tip of said third leg is aligned with the end of the second arm, and
        the tips of said first, second, and third legs define the reference plane for the human body structure.

2. The surgical instrument of claim 1 wherein said first, second, and third legs are configured so that the nominal plane defined by said frame is parallel to the reference plane defined by the tips of said first, second, and third legs.

3. The surgical instrument of claim 1 wherein a length of the first arm is adjustable relative to the hub of said frame, such that a spacing between the tip of said first leg and the tip of said second leg is adjustable.

4. The surgical instrument of claim 3 wherein a length of the second arm is adjustable relative to the hub of said frame, such that a spacing between the tip of said first leg and the tip of said third leg is adjustable.

5. The surgical instrument of claim 4 wherein a spacing between the tips of a first pair of said first, second, and third legs is adjusted to be a predetermined proportion of a spacing between the tips of a second pair of said first, second, and third legs.

6. The surgical instrument of claim 1 wherein said first and second legs are removably attached to the first and second arms of said frame, and said third leg is removably attached to said offset adapter.

7. The surgical instrument of claim 1 wherein said third leg has an end opposite the tip of said third leg, and said offset adapter is configured to position the end of said third leg away from the end of the second arm of said frame.

8. The surgical instrument of claim 1 wherein said guide is adjustably mounted to said frame, and said frame includes a first scale for positioning said guide at a desired angle within the nominal plane defined by said frame.

9. The surgical instrument of claim 8 wherein said frame includes a second scale for positioning said guide at a desired angle orthogonal to the nominal plane defined by said frame.

10. The surgical instrument of claim 1 wherein the axis in space relative to the reference frame identifies a desired orientation of an acetabular component.

11. The surgical instrument of claim 1 wherein the offset adapter includes a split collar having a bore for receiving said third leg.

12. The surgical instrument of claim 11 wherein the offset adapter includes means for securing said third leg in the bore.

13. The surgical instrument of claim 1 wherein the offset adapter has a curved shape.

14. The surgical instrument of claim 1 wherein the predetermined angle is 20 to 30 degrees.

15. The surgical instrument of claim 1 wherein one or more of said first, second, or third legs is hollow.

* * * * *

UNITED STATES PATENT AND TRADEMARK OFFICE
CERTIFICATE OF CORRECTION

| | |
|---|---|
| PATENT NO. | : 10,004,752 B2 |
| APPLICATION NO. | : 13/692270 |
| DATED | : June 26, 2018 |
| INVENTOR(S) | : Stephen B. Murphy |

It is certified that error appears in the above-identified patent and that said Letters Patent is hereby corrected as shown below:

In the Specification

Column 3, Line 35 reads:
"conduit 109, and held there by any of a number of well-"
Should be corrected to read:
-- conduit 107, and held there by any of a number of well- --

Signed and Sealed this
Third Day of September, 2019

Andrei Iancu
*Director of the United States Patent and Trademark Office*